United States Patent [19]

Friary et al.

[11] Patent Number: 4,725,596
[45] Date of Patent: Feb. 16, 1988

[54] PYRIMIDINE DERIVATIVES HAVING ANTI-ALLERGY, ANTI-INFLAMMATORY AND IMMUNO SUPPRESSANT ACTIVITY

[75] Inventors: Richard J. Friary, West Orange; Sidney R. Smith, Ridgewood; Marvin I. Siegel, Woodbridge, all of N.J.

[73] Assignee: Schering Corporation, Kenilworth, N.J.

[21] Appl. No.: 897,169

[22] Filed: Aug. 15, 1986

Related U.S. Application Data

[63] Continuation-in-part of Ser. No. 729,334, May 1, 1985, abandoned.

[30] Foreign Application Priority Data

May 1, 1986 [WO] PCT Int'l Appl. .............. PCT/US86/00899

[51] Int. Cl.⁴ ............... A61K 31/505; C07D 471/14; C07D 487/14
[52] U.S. Cl. .................................. 514/214; 514/242; 514/250; 514/267; 540/479; 540/559; 544/182; 544/251
[58] Field of Search ............... 544/251, 182; 540/479, 540/559; 514/267, 250, 214, 242

[56] References Cited

U.S. PATENT DOCUMENTS

| | | | |
|---|---|---|---|
| 3,859,289 | 1/1975 | Hardtmann | 544/251 |
| 3,887,559 | 6/1975 | Hardtmann | 540/559 X |
| 3,905,976 | 9/1975 | Hardtmann | 544/250 |
| 3,975,386 | 8/1976 | Hardtmann | 544/91 |

FOREIGN PATENT DOCUMENTS

2257376 5/1973 Fed. Rep. of Germany ...... 514/267
2402454 7/1974 Fed. Rep. of Germany .

OTHER PUBLICATIONS

Hardtmann, et al., J. Med. Chem., vol. 18, No. 5, pp. 447-453 (1975).
Coppola, et al., J. Heterocyclic Chem., vol. 22, No. 1, 01-02/85, pp. 193-206.

*Primary Examiner*—Donald G. Daus
*Assistant Examiner*—Diana G. Rivers
*Attorney, Agent, or Firm*—Richard C. Billups; James R. Nelson; Stephen I. Miller

[57] ABSTRACT

Certain pyrimidine derivatives are useful in treating allergic, inflammatory and hyperproliferative skin diseases and in suppressing the immune response. Methods for preparing the compounds and methods for their use are also described.

14 Claims, No Drawings

PYRIMIDINE DERIVATIVES HAVING ANTI-ALLERGY, ANTI-INFLAMMATORY AND IMMUNO SUPPRESSANT ACTIVITY

This application is a continuation-in-part of U.S. application Ser. No. 729,334, filed May 1, 1985, now abandoned, the benefit of which is claimed pursuant to 35 U.S.C. 120.

This invention relates to novel pyrimidine derivatives. These compounds are useful as anti-allergy anti-inflammatory, and immuno-suppressing agents.

U.S. Pat. Nos. 3,859,289 and 3,975,386 and German Offenlegungsschrift No. 2,402,454 describe certain 10-phenyl-2,3-dihydroimidazo[1,2-a]pyrido[2,3-d]pyrimidin-5(10H)-ones and 11-phenyl-2,3,4,11-tetrahydropyrido[2,3-a]pyrimidin-6(6H)-ones useful as hypotensive agents. However, the method for synthesizing such 10- and 11-aryl substituted compounds using an aryl halide reactant as disclosed in the above patents is believed to be inoperative because aryl halides fail completely to react with the 3,4-dihydro-1,3-dioxo-1H-pyrido[2,3-d][1,3]oxazine intermediates under the conditions disclosed. Thus, since the 10-phenyl-2,3-dihydroimidazo[1,2-a]pyrimido[2,3-d]pyrimidin-5(10H)-ones and 11-aryl-2,3,4,11-tetrahydropyrido[2,3-d]pyrimido[1,2-a]pyrimidin-6(6H)-ones named in the above patent publications cannot be synthesized according to the processes disclosed therein, they have not existed in the prior art previous to the invention described herein.

SUMMARY OF THE INVENTION

The novel compounds have structural formula I:

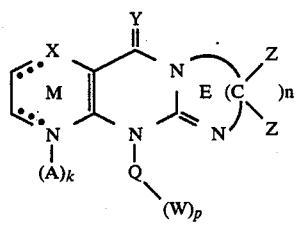

wherein
X is CH, CH$_2$, N or N(A)$_k$;
Y is O or S;
Q is phenyl, pyridyl, furyl, thienyl, pyrrolyl, isoxazolyl, isothiazolyl or pyrazolyl;
W is lower alkyl, hydroxyl, halogen, nitro, amino, lower alkoxy, R$^a$, OR$^a$, NHR$^a$, wherein R$^a$ is acyl having from 1 to 6 carbon atoms, R$^b$, COR$^b$, OR$^b$, OCOR$^b$, OR$^b$-lower alkyl, S(O)$_m$R$^b$ wherein m is 0, 1 or 2 and R$^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl and m is 0, 1 or 2, SO$_2$NR$^d$R$^e$, wherein R$^d$ and R$^e$ independently are hydrogen, lower alkyl or R$^b$ as defined herein, NHR$^c$ or N(R$^c$)$_2$, wherein R$^c$ is as defined above;
the dotted lines (- - - -) represent optional double bonds in ring "M";
k is 0 or 1;
p is 0, 1, 2, 3, 4 or 5 provided that when Q is other than phenyl p is 0;
A is hydrogen, alkyl having from 1 to 6 carbon atoms, CH$_2$CH$_2$OH, COR$^f$, SO$_2$R$^f$ wherein R$^f$ is hydrogen, lower alkyl, phenyl or substituted phenyl, or (CH$_2$)$_q$R$^g$, wherein q is 1, 2, 3, 4 or 5 and R$^g$ is carboxyl or NR'$_2$, wherein R' is hydrogen or lower alkyl;
n is 2 to 6 provided that when n is 3, ring E has no double bond between carbon atoms;
each z is independently hydrogen, lower alkyl or z's on adjacent carbon atoms together from a double bond; and
ring M is unsubstituted or substituted at its carbon atoms by lower alkyl groups.

A preferred subgenus of compounds is that wherein X is CH and Y is O.

A second preferred subgenus of compounds is that wherein X is CH and Y is S.

A third preferred subgenus of compounds is that wherein X is N and Y is O.

A fourth preferred subgenus of compounds is that wherein Q is phenyl.

Preferred species havig structural formula I are those shown below (melting points and recrystallization solvents are given):

Compounds having the formula:

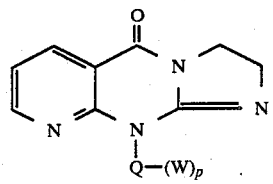

wherein —Q—(W)$_p$ is

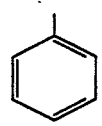

307–310° C. (MeOH—CHCl$_3$)

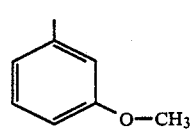

308–308.5° C. (MeOH—CHCl$_3$)

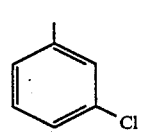

305–307° C. (MeOH—CHCl$_3$)

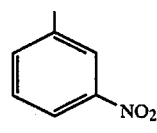

286–298° C. (CHCl$_3$—Et$_2$O)

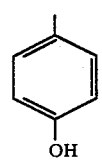

316° C. (MeOH—Et$_2$O)

-continued

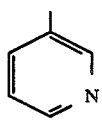 273.5–274.5° C. (MeOH)

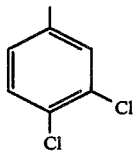 252.5–254° C. (MeOH—CHCl₃)

Compounds having the formula:

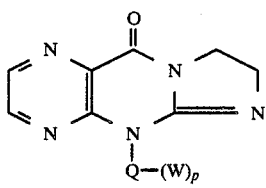

wherein —Q—(W)$_p$ is:

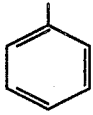 315° C. (CHCl₃—pet. ether)

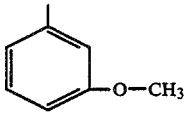 >315° C. (CH₂Cl₂—pet. ether)

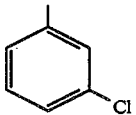 >315° C. (CH₂Cl₂—pet. ether)

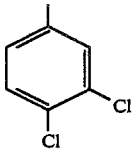 267–268° C. (CH₂Cl₂—pet. ether)

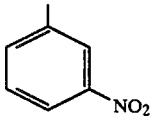 278–283° C. (CHCl₃—Et₂O).

Compounds having the formula:

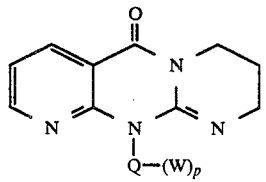

wherein —Q—(W)$_p$ is

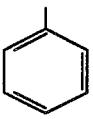 252–254° C. (CHCl₃—EtO)

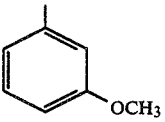 230–231° C. (CH₂Cl₂—Et₂O)

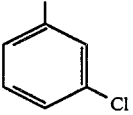 235–237° C. (CH₂Cl₂—Et₂O)

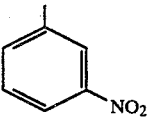 243–245° C. (CHCl₃—Et₂O)

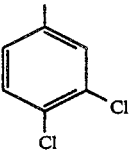 234–236° C. (CHCl₃—Et₂O)

Compounds having the formula:

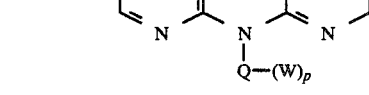

wherein —Q—(W)$_p$ is

 268–271° C. (CHCl₃—Et₂O) (hemihydrate)

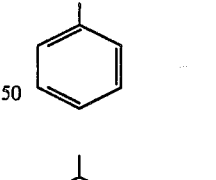 228–229° C. (CHCl₃—Et₂O).

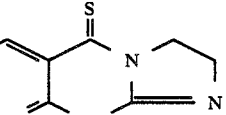 293–296° C. (CHCl₃—Et₂O).

-continued

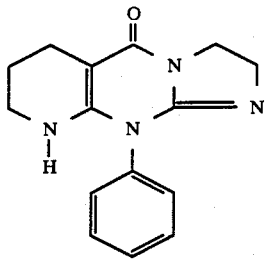
248–250.5° C.
(EtOAc—MeOH).

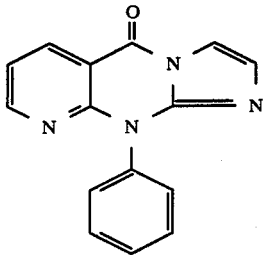
289–290° C. (CHCl₃—Et₂O).

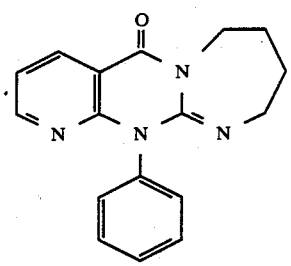
217–220° C.
CCHCl₃—pet. ether)

A preferred compound is 10-(3-nitrophenyl)-2,3-dihydro-imidazo[1,2-a]pyrazino[2,3-d]pyrimidin-5(10H)-one.

Another aspect of the invention is a pharmaceutical composition which comprises a compound having structural formula I in combination with a pharmaceutically acceptable carrier.

Another aspect of the invention is a method for treating allergic reactions in a mammal which comprises administering an anti-allergic effective amount of a compound of formula I to said mammal.

Another aspect of the invention is a method for treating inflammation in a mammal which comprises administering an anti-inflammatory effective amount of a compound of formula I to said mammal.

Still another aspect of the invention is a method for treating hyperproliferative skin diseases (e.g., psoriasis, lichenified eczema or seborrhoeic dermatitis) in mammals which comprises topically administering an effective amount of a compound of formula I to said mammal.

Yet another aspect of the invention is a method for suppressing the immune response in mammals which comprises administering an immuno-suppressant effective amount of a compound of formula I to said mammal.

DETAILED DESCRIPTION OF THE INVENTION

The compounds of formula I may be prepared according to the following reaction schemes:

A. To produce a compound of formula I wherein the dotted lines (- - - -) in ring M represent double bonds, a compound of the formula

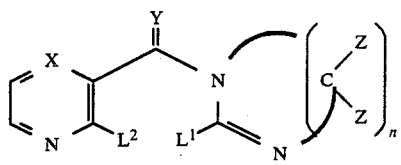

wherein X, Y, and Z and n are as defined previously and $L^1$ and $L^2$ are leaving groups, is reacted with a compound of the formula

wherein Q, W, and p are as defined previously.

Materials of formula IV may be produced by the following reactions:

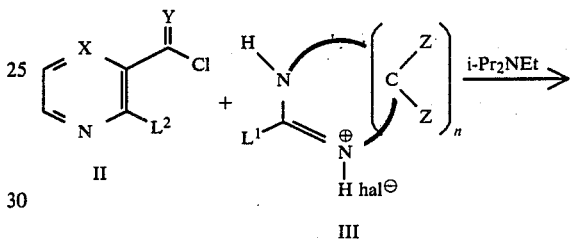

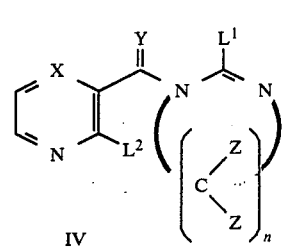

wherein X, Y, Z, $L^1$, $L^2$, and n are as previously defined and hal is Cl, Br, F, or I.

The choice of leaving groups $L^1$ and $L^2$ is not critical. $L^1$ and $L^2$ can, for example, be independently chosen from —S—CH₃, —S—loweralkyl, —SOCH₃, —SO₂CH₃, halogen, —SO₂R, O₃SR (wherein R is loweralkyl, aryl, or aralkyl), or —OSO₂CF₃.

The reaction of known starting materials having structural formulas II and III with an organic base such as diisopropylethylamine in a nonreactive solvent such as methylene chloride for 15–18 hrs. at a temperature of 0°–25° C. will produce the compounds having structural formula IV.

Exemplary of such starting materials having structural formula II are 2-chloronicotinoyl chloride wherein X is CH and 2-chloropyrazin-3-carbonyl chloride wherein X is N, and those having structural formula III 2-methylthioimidazoline hydroiodide wherein n is 2, all of which are available commercially. A starting material having structural formula III is 2-methylthio-3,4,5,6-tetrahydropyrimidine hydroiodide wherein n is 3 and z is hydrogen may be prepared, for example, as described in W. G. Hatton, J. Am. Chem. Soc., 78, 1618 (1956).

The reaction of compounds having structural formula IV with a substituted phenylamine or a heteroarylamine (formula IV(a)) in a methanol/glacial acetic acid or a t-butyl alcohol/p-toluenesulfonic acid monohydrate solution refluxing for 4.5–24 hours will produce the compounds of the invention having structural formula V.

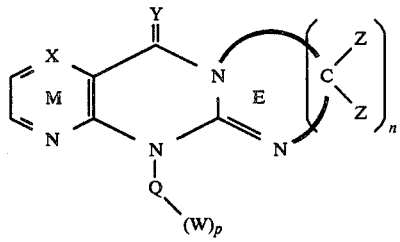

B. To produce a compound of formula I wherein there is a single bond at the locations of the dotted lines (- - - -) in ring M a compound of formula I having a double bond at the locations of the dotted lines (i.e. a compound of formula V) is subjected to hydrogenation.

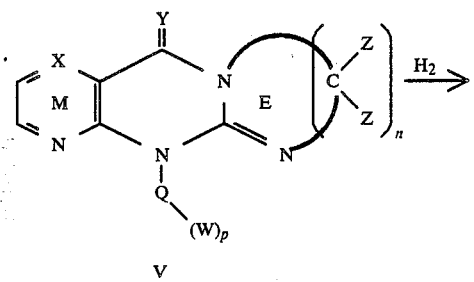

The hydrogenation may be carried out over 10% Pd/C catalyst in glacial acetic acid or other suitable solvent at about room temperature.

C. To produce a compound of formula I wherein Y is S, a compound of formula I wherein Y is O is reacted with $P_2S_5$ or Lawesson's reagent, which has the formula:

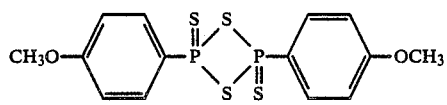

The reaction may take place at elevated temperature in pyridine or other suitable solvent.

D. To produce a compound of formula I wherein ring E has a double bond between carbon atoms, a compound of formula I wherein ring E has no double bond between carbon atoms is subjected to dehydrogenation. Dehydrogenation may be accomplished by refluxing with an appropriate oxidizing agent such as barium manganate in methylene chloride or other suitable solvent, such as chloroform, $CCl_4$, etc. for 42 hours.

E. To make a compound of formula I wherein the dotted line (- - - -) represent double bonds in ring M, and Y is O, a compound of formula X

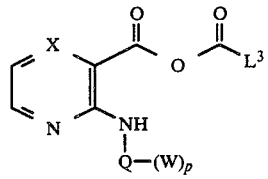

is reacted with a compound of formula III

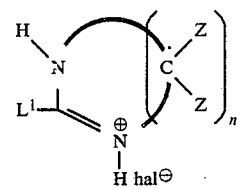

wherein $L^1$, X, Q, W, p and Z are as previously defined hal is Cl, F, Br, or I, and $L^3$ is a leaving group selected from lower alkoxy, aryloxy, or aralkoxy.

Compounds of formula X may be made by the following reaction

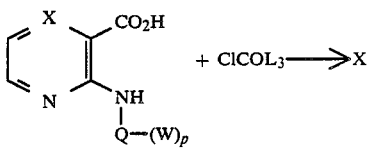

wherein X, Q, W, p, and $L_3$ are a previously defined. The above reaction is carried out in a inert solvent, e.g. dichloromethane chloroform or $CCl_4$, and a tertiary amino base at about 0° to 25° C.

F. To produce a compound of formula I wherein a is other than hydrogen and k is 1, a compound of formula I wherein A is hydrogen and k is 1, and wherein the dotted lines (- - - - -) are not double bonds is acylated or alkylated. Example of suitable alkylating and acylating agents are methyl iodide and acetic anhydride. Suitable solvents and bases for alkylation are respectively acetone or dimethylformamide, and potassium carbonate or sodium hydride. Suitable solvents and bases for acylation are respectively dichloromethane or chloroform, and triethylamine or diisopropylethylamine.

When utilized herein and in the appended claims the below listed terms, unless specified otherwise, are defined as follows:

halogen means fluorine, chlorine, bromine and iodine;

lower alkyl means straight or branched chain alkyls of 1 to 4 carbons, e.g. methyl, ethyl, propyl, isopropyl, n-butyl, t-butyl, pentyl, neopentyl, n-hexyl and the like;

lower alkoxy means straight or branched chain alkoxy of 1 to 6 carbons, e.g. methoxy, ethoxy, isopropoxy, t-butoxy, n-hexoxy and the like; acyl means lower alkyl carbonyl; and aryl means phenyl, naphthyl and other saturated aromatic groups which may be substituted.

Certain compounds of the invention can exist in isomeric forms. For example, optical isomers can occur when saturated carbon atoms of rings M and E have a single alkyl group substituent. Position isomers exist in view of the definition for structural formula I which includes heterocyclic rings that can form bonds with substituents at different positions in their rings. The invention contemplates all such isomers both in pure form and in admixture, including racemic mixtures.

The compounds of the invention having structural formula I can exist in unsolvated as well as solvated forms, including hydrated forms. In general, the solvated forms, with pharmaceutically acceptable solvates such as water, ethanol and the like are equivalent to the unsolvated forms for purposes of the invention.

Certain compounds of the invention are acidic in nature, e.g. those compounds which possess a carboxyl group or phenolic hydroxyl group. These compounds can form pharmaceutically acceptable salts. Examples of such salts are the sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain compounds of the invention are basic in nature, e.g. those possessing a partially reduced "M" ring as defined above. These compounds can form pharmaceutically acceptable acid addition salts. Examples of such salts are the hydrochloride, sulfate, phosphate and the like.

The compounds of the invention which possess an aromatic "M" ring, as defined above can also form quaternary salts at an aromatic "M" ring nitrogen atom.

The compounds of the invention can also form quaternary salts of any of the nitrogen atoms in the two fused rings other than ring M.

All such acid, base and quaternary salts are considered equivalent to the free forms of the corresponding compounds for purposes of the invention.

The compounds of this invention can be used to treat allergy caused diseases and their preferred uses are for treating contact dermatitis, anaphylactic bronchospasm and allergic chronic obstructive lung diseases. Chronic obstructive lung disease as used herein means disease conditions in which the passage of air through the lungs is obstructed or diminished such as is the case in asthma, bronchitis and the like.

The anti-allergy activity of this invention is identified by tests which measure a compound's inhibition of anaphylactic bronchospasm in sensitized guinea pigs having antigen induced, slow-reacting substance of anaphylaxis (SRS-A)-mediated bronchoconstriction.

Allergic bronchospasm was measured in actively sensitized guinea pigs by a modification of the procedure of Konzett and Rossler, Arch. Exptl. Pathol. Pharmakol., 194, pp. 71-74 (1940).

Male Hartley guinea pigs were sensitized with 5 mg ovalbumin injected ip and 5 mg injected sc in 1 ml saline on day 1 and 5 mg ovalbumin injected ip on day 4. The sensitized animals were used 3-4 weeks later.

To measure anaphylactic bronchospasm, sensitized guinea pigs were fasted overnight and the following morning were anesthetized with 0.9 ml/kg ip of dialurethane. The trachea and jugular vein were cannulated and the animals were ventilated by a Harvard rodent respirator. A side arm to the tracheal cannula was connected to a Harvard pressure transducer to obtain a continuous measure of intratracheal pressure. An increase in intratracheal pressure was taken as a measure of bronchoconstriction.

Each guinea pig was injected iv with 1 mg/kg propranolol, 5 mg/kg indomethacin and 2 mg/kg mepyramine given together in a volume of 1 ml/kg. Fifteen minutes later, the animals were challenged with antigen (0.5 percent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge. For example, the compound 10-phenyl-2,3-dihydroimidazo[1,2-a]pyrido[2,3-d]pyrimidin-5-(10$\underline{H}$)-one was found to inhibit anaphylactic bronchospasms in such test procedure when given at oral dose of 2 mg/kg. Said compound was also found to inhibit allergen-induced histamine and SRS-A release from guinea pig lung tissue.

The compounds are effective non-adrenergic, non-anticholinergic antianaphylactic agents. When administered orally, they are active at doses from about 0.2 to 10 mg/kg of body wieght; when administered parenterally, e.g., intravenously, the compounds are active at dosages of from about 0.1 to 5 mg/kg body weight; and when administered by inhalation (aerosol or nebulizer) the compounds are active at dosages of about 0.1 to 5 mg per puff, and one to four puffs may be taken every 4 hours.

The compounds of this invention are also useful for the treatment of inflammation; thus, they are useful for the treatment of: arthritis, bursitis, tendonitis, gout and other inflammatory conditions. The anti-inflammatory use of the compounds of the present invention may be demonstrated by the Reversed Passive Arthus Reaction technique as set forth below. The potency of the compounds is determined using indomethacin as the standard. On the basis of the test results, a dosage range of 0.02 to about 20 mpk in divided doses taken at about 4 hour intervals is recommended.

The dosage to be administered and the route of administration depends upon the judgment of the attending clinician taking into account the potency of the particular compound used, the age and general health of the patient and the severity of the inflammatory conditions.

Reversed Passive Arthus Reaction (RPAR)

Animals, Materials and Methods

Male Lewis inbred albino rats weighing 180-220 grams obtained from Charles River Breeding Laboratories are used in these experiments. The rats are housed 3 animals/cage and food and water are allowed ad libitum. The animals are numbered 1-3 in each cage and color marked for identification purposes.

Drug and Reagent Preparation

All reagents and drugs are prepared just prior to the study. Crystallized and lyophilized bovine serum albumin (BSA), obtained from Sigma Chemical Company, is solubilized without shaking in cold, sterile, pyrogen-free saline (10 mg/ml). Lyophilized anti-bovine serum albumin (IgG Fraction), obtained from Cappel Laboratories, is suspended in sterile distilled water and diluted with cold pyrogen-free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Drug Administration and Induction of Inflammation

Groups of animals (6/group) are dosed with drug in MC by gavage one hour prior to sensitization with BSA. Controls are given MC alone and drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after dosing the animals are lightly anesthetized with ether and "sensitized" by injecting into the penile vein 0.2 ml of PFS containing 1.0 mg of BSA. One hour later they are injected in the plantar region of one hind paw with 0.1 ml of PFS containing 0.1 mg of the anti-bovine serum albumin. Immediately after the subplantar injection, the injected paw is dipped (up to the lateral maleolus) into the mercury well of a plethysmograph. The volume of mercury displaced is converted to weight and recorded. This value is considered to be the control paw volume for the animal. Paw volumes are also recorded with a plethysmograph during the development of the inflammation at 2 and 4 hours post-challenge.

Results

Results are expressed by the change in paw volume ($\Delta$ paw volume) from the control reading for each animal to that recorded 2 and 4 hours post-challenge. All drug treated groups are compared to the MC control for significant difference with an analysis of variance. Differences from control in drug-treated groups are expressed as percent change from control.

The compounds of the invention were also found to possess anti-inflammatory activity from in vivo oral activity in therapeutic and prophylactic adjuvant-induced arthritis assays in rats and from in vivo oral activity in RPAR-Pleural Cavity assays in rats.

The compounds of formula I are useful in the treatment of hyperproliferative skin disease, e.g., psoriasis, which utility may be demonstrated by the Arachiodonic Acid Mouse Ear Test as described below.

Arachidonic Acid Mouse Ear Test, Materials and Methods

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by applying 10 $\mu$l of AA to both surfaces of one ear (4 mg total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol*, 82, pp 367-371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean $\pm$ standard error and all possible comparisons are made via Duncan's Multiple Range Statistic. The compound 10-(3-nitrophenyl)-2,3-dihydroimidazo[1,2-a]pyrazino[2,3-d]pyrimidin-5(10H)-one (Compound A) showed 44% inhibition at a dose of 0.5 mg/ear.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating said individual psoriatic patient may vary, but those skilled in the art of medicine will be able to recognize these variations and adjust the course of therapy accordingly.

Included within the invention are preparation for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, perferably from about 0.1 percent to about 5 percent, is applied several times daily to the affected skin until the condition has improved. Topical applications may then be continued at less frequent intervals (e.g. once a day) to control mitosis in order to prevent return of severe disease conditions.

The compounds are useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(B6AF1) male mice were injected intravenously with parental (C57B1/6J) spleen and lymph node cells. Compound A was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of Compound A administered to the mice in the experimental group is measured by comparing the spleen weight of the untreated and treated GVH animal with that of the syngeneic control. Compound A reduced spleen weight by 44%, 36% and 42% as compared to the untreated animals at doses of 25, 50 and 100 mg/kg, respectively.

SPLENIC ATROPHY

The immunosuppressive activity of the compounds may also be shown by a decrease in spleen weight after dosing $BDF_1$ mice orally with the drug for seven (7) consecutive days. The mice are sacrificed on the eighth day. The percent decrease in spleen weight is measured for each dosage level. In this procedure Compound A provided a 13%, 24% and 30% spleen weight decrease at dosage levels of 25, 50 and 100 mg/kg, respectively.

The usual dosage range for the compounds of formula I for providing immunosuppression activity in a 70 kg mammal is an oral dose of about 0.1 to 250 mg/kg, preferably 0.1 to 150 mg/kg, in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formula I can be administered in unit dosage forms such as tablets, capsules, pills, powders, granules, sterile parenteral solutions or suspensions, suppositories, transdermal compositions and the like. Such dosage forms are prepared according to standard techniques well known in the art.

For preparing pharmaceutical compositions from the compounds described by this invention, inert, pharmaceutically acceptable carriers can be either solid or liquid. Solid form preparations include powders, tablets, dispersible granules, capsules and cachets. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethycellulose, a low melting wax, cocoa butter and the like.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made.

The quantity of active compound in a unit dose of preparation may be varied from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples illustrate the preparation of the compounds of this invention.

PREPARATIVE EXAMPLE A

Compounds Having Structural Formula IV

An equimolar solution of compounds having structural formula II and III and of diisopropylethylamine (2 mole/mole of II or III) dissolved in dichloromethane (2-3 ml/mmole of II or III) is allowed to stir 15-18 hrs. in a cooling bath (0°-25° C.). The solution is washed sequentially with $H_2O$, dilute aq. $NaHCO_3$ and with $H_2O$. The solution is dried ($Na_2SO_4$ or $MgSO_4$) and filtered. The solvent is evaporated to give a compound having structural formula IV which can be used directly in the next step or can be purified by recrystallization if desired.

Utilizing 2-chloronicotinoyl chloride (Chemo Dynamics, Inc.) for II and 2-methylthioimidazoline hydroiodide (Aldrich Chemical Co.) for III in preparative example A gives 1-(2-chloro-3-pyridylcarbonyl)-2-methylthio-4,5-dihydroimidazoline, m.p. 105.0°–106.0° C. (from i-PrOAc).

Utilizing 2-chloronicotinoyl chloride and 2-methylthio-3,4,5,6-tetrahydropyrimidine hydroiodide (W. G. Hatton, *J. Am. Chem. Soc.* 78, 1618 (1956)) in preparative example A gives 1-(2-chloro-3-pyridylcarbonyl)-2-methylthio-1,4,5,6-tetrahydropyrimidine, m.p. 133°–134° C. (from $CH_2Cl_2$-pet. ether).

Utilizing 2-chloropyrazin-3-carbonyl chloride (Chemo Dynamics, Inc.) and 2-methylthioimidazoline hydroiodide in preparative example A gives 1-(2-chloro-3-pyrazinylcarbonyl)-2-methylthio-4,5-dihydroimidazoline, m.p. 102°–105° C. (from $CHCl_3$-$CCl_4$).

Utilizing 2-chloropyrazin-3-carbonyl chloride and 2-methylthio-3,4,5,6-tetrahydropyrimidine hydroiodide in preparative example A gives 1-(2-chloro-3-pyrazinylcarbonyl)-2-methylthio-1,4,5,6-tetrahydropyrimidine, m.p. 137°–140° C. (from $CHCl_3$—$Et_2O$).

EXAMPLE 1

Reflux a equimolar mixture of a compound having structural formula IV and a substituted phenylamine dissolved in methanol (2.1–2.6 ml/mmole of IV) and glacial acetic acid (1.5–1.8 moles/mole of IV) 4.5–24 hrs, and cool to room temperature. Evaporate the methanol and wash a $CHCl_3$ solution of the residue with dilute aqueous $NaHCO_3$ solution and with $H_2O$. Dry the $CHCl_3$ solution ($Na_2SO_4$ or $MgSO_4$) and filter. Concentrate the $CHCl_3$ solution, treat with charcoal or chromatograph as needed, and finally crystallize to give the desired product having structural formula V.

By utilizing the appropriate starting materials in the procedure described in example 1, the following products are obtained:

10-phenyl-2,3-dihydroimidazo[1,2-a]pyrido[2,3-d]pyrimidin-5(10H)-one, m.p. 307°–310° C. (MeOH—$CHCl_3$);

10-(3-methoxyphenyl)-2,3-dihydroimidazo[1,2-a]pyrido[2,3-d]pyrimidin-5(10H)-one, m.p. 308°–308.5° C. (MeOH—CHCl₃);

10-(3-chlorophenyl)-2,3-dihydroimidazo[1,2-a]pyrido[2,3-d]pyrimidin-5(10H)-one, m.p. 305°–307° C. (MeOH—CHCl₃);

10-(3,4-dichlorophenyl)-2,3-dihydroimidazo[1,2-a]pyrido[2,3-d]pyrimidin-5(10H)-one, m.p. 252.5°–254.0° C. (MeOH—CHCl₃);

10-phenyl-2,3-dihydroimidazo[1,2-a]pyrazino[2,3-d]pyrimidin-5(10H)-one, m.p. >315° C. (CHCl₃-pet. ether);

10-(3-methoxyphenyl)-2,3-dihydroimidazo[1,2-a]pyrazino[2,3-d]pyrimidin-5(10H)-one, m.p. >315° C. (CH₂Cl₂-pet. ether);

10-(3-chlorophenyl)-2,3-dihydroimidazo[1,2-a]pyrazino[2,3-d]pyrimidin-5(10H)-one, m.p. >315° C. (CH₂Cl₂-pet. ether);

10-(3,4-dichlorophenyl)-2,3-dihydroimidazo[1,2-a]pyrazino[2,3-d]pyrimidin-5(10H)-one, m.p. 267°–268° C. (CH₂Cl₂-pet. ether);

EXAMPLE 2

This procedure is identical to example 1 except that t-butyl alcohol and p-toluenesulfonic acid monohydrate are used in place of methanol and glacial acetic acid, respectively. Ratios of 2.5–5 ml of t-butyl alcohol per mmole of IV and of 0.05 moles of p-toluenesulfonic acid monohydrate per mole of IV are used.

By utilizing the appropriate starting materials in the procedure described in example 2 the following products are obtained:

10-(3-nitrophenyl)-2,3-dihydroimidazo[1,2-a]pyrido[2,3-d]pyrimidin-5(10H)-one, m.p. 286°–287° C. (CHCl₃-Et₂O);

10-(3-nitrophenyl)-2,3-dihydroimidazo[1,2-a]pyrazino[2,3-d]pyrimidin-5(10H)-one, m.p. 278°–283° C. (CHCl₃—Et₂O);

11-phenyl-2,3,4,11-tetrahydropyrido[2,3-d]pyrimido[1,2-a]pyrimidin-6(6H)-one, m.p. 252°–254° C. (CHCl₃—Et₂O);

11-(3-methoxyphenyl)-2,3,4,11-tetrahydropyrido[2,3-d]pyrimido[1,2-a]pyrimidin-6(6H)-one, m.p. 230°–231° C. (CH₂Cl₂—Et₂O);

11-(3-chlorophenyl)-2,3,4,11-tetrahydropyrido[2,3-d]pyrimido[1,2-a]pyrimidin-6(6H)-one, m.p. 235°–237° C. (CH₂Cl₂—Et₂O);

11-(3-nitrophenyl)-2,3,4,11-tetrahydropyrido[2,3-d]pyrimido[1,2-a]pyrimidin-6(6H)-one, m.p. 243°–245° C. (CHCl₃—Et₂O);

11-(3,4-dichlorophenyl)-2,3,4,11-tetrahydropyrido[2,3-d]pyrimido[1,2-a]pyrimidin-6(6H)-one, m.p. 234°–236° C. (CHCl₃—Et₂O);

10-(4-hydroxyphenyl)-2,3-dihydroimidazo[1,2-a]pyrido[2,3-d]pyrimidin-5(10H)-one, m.p. 316° C. (MeOH—Et₂O);

11-phenyl-2,3,4,11-tetrahydropyrimido[1,2-a]pyrazino[2,3-d]pyrimidin-6(6H)-one, hemihydrate, m.p. 268°–271° C. (CHCl₃—Et₂O);

11-(3-nitrophenyl)-2,3,4,11-tetrahydropyrimido[1,2-a]pyrazino[2,3-d]pyrimidin-6(6H)-one, m.p. 228°–229° C. (CHCl₃—Et₂O); and 10-(3-pyridyl)-2,3-dihydroimidazo[1,2-a]pyrido[2,3-d]pyrimidin-5-(10H)-one, m.p. 273.5°–274.5° C. (MeOH).

EXAMPLE 3

10-PHENYL-2,3-DIHYDROIMIDAZO[1,2-a]PYRIDO[2,3-d]PYRIMIDIN-5(10H)-THIONE

Reflux a mixture of 10-phenyl-2,3-dihydroimidazo[1,2-a]pyrido[2,3-d]pyrimidin-5(10H)-one (10.5 g.), phosphorous pentasulfide (23.9 g) and pyridine (265 ml.) for 5 hrs. Cool the resulting solution and pour into H₂O(5l.). Collect the precipitate, wash with water, dry and crystallize from CHCl₃—Et₂O to yield 10-phenyl-2,3-dihydroimidazo[1,2-a]pyrido[2,3-d]pyrimidin-5(10H)-thione, m.p. 293°–296° C.

EXAMPLE 4

10-PHENYL-2,3,6,7,8,9-HEXAHYDROIMIDAZO[1,2-a]PYRIDO[2,3-d]PYRIMIDIN-5(10H)-ONE

Hydrogenate a mixture of 10% Pd/C (2.5 g), 10-phenyl-2,3-dihydroimidazo[1,2-a]pyrido[2,3-d]pyrimidin-5(10H)-one (5 g) and glacial acetic acid (125 ml) at 60 psi in a Paar apparatus for 24 hrs. at 25° C. Filter the mixture and evaporate the solvent of the filtrate. Dissolve the residue in 1N NaHCO₃ (50 ml), neutralize with additional solid NaHCO₃ and extract with CHCl₃. Wash combined extracts with H₂O, dry and filter. Evaporate solvent of the filtrate and crystallize the residue from EtOAc—MeOH to give 10-phenyl-2,3,6,7,8,9-hexahydroimidazo[1,2-a]-pyrido[2,3-d]pyrimidin-5(10H)-one, m.p. 248.0°–250.5° C.

EXAMPLE 5

10-PHENYL-IMIDAZO[1,2-a]PYRIDO[2,3-d]PYRIMIDIN-5(10H)-ONE

Reflux a mixture of barium manganate (15 g.), methylene chloride (400 ml) and 10-phenyl-2,3-dihydroimidazo[1,2-a]pyrido[2,3-d]pyrimidin-5(10H)-one (1g) 42 hrs. Cool the resulting mixture and filter through diatomaceous earth and charcoal. Wash the solids on the filter with methylene chloride and evaporate the solvent of the combined filtrates. Chromotograph the residue over silica gel and elute the desired product with chloroform. Crystallize to obtain from chloroform-ether 10-phenyl-imidazo[1,2-a]pyrido[2,3-d]pyrimidin-5(10H)-one, m.p. 289°–290° C.

EXAMPLE 6

Add triethylamine (2.5 g) to a 0°-suspension of 2-phenylamino-nicotinic acid (5.35 g) and a solvent of dichloromethane (100 ml), and then add a solution of ethyl chloroformate (2.7 g) dissolved in dichloromethane (25 ml). Stir the resulting mixture for 2 hours at about 3° in an atmosphere of nitrogen, using an ice bath for cooling. At this point the compound ethyl-2-phenylaminonicotinoyl carbonate (formula X), m.p. 137.5–139.5 (CHCl₃-pet. ether) may be isolated, if desired. However in this case the material of formula X was used in situ. Add triethylamine (2.5 g) again, and also add 2-methylthio-2-imidazoline hydriodide (6.1 g). Allow the resulting reaction mixture to stir 2 hours at 3° and 20 hours at an ambient temperature of about 25°. Wash the solution with dilute aqueous sodium bicarbonate and with water. Extract the organic solution with two portions of dilute aqueous hydrochloric acid, and combine the extracts with one another. Cool the united extracts and basify them with 50% aqueous sodium hydroxide solution, collecting the resulting precipitate on a filter. Wash the precipitate with water, dry and crystallize it from MeOH—CHCl₃.

By using appropriate starting materials in the procedure described in this example, the following products are obtained:

10-phenyl-2,3-dihydroimidazo[1,2-a]pyrido[2,3-d]pyrimidin-5(10H)-one (Also prepared in Example 1) m.p. 307°–310° C. (MeOH—CHCl₃).

12-phenyl-2,3,4,5-tetrahydropyrido[2',3':4,5-]pyrimido[1,2a][1,3]diazepine-7(12H)-one, m.p. 217°–220° (CHCl₃-pet. ether)

We claim:

1. A compound having the structural formula I:

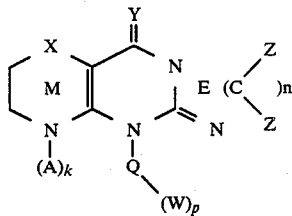

or a pharmaceutically acceptable solvate, hydrate or salt thereof, wherein

X is N or N(A)$_k$;

Y is O or S;

Q is phenyl, pyridyl, furyl, thienyl, pyrrolyl, isoxazolyl, isothiazolyl or pyrazolyl;

W is lower alkyl, hydroxyl, halogen, nitro, amino, lower alkoxy, R$^a$, OR$^a$, NHR$^a$ wherein R$^a$ is acyl having from 1 to 6 carbon atoms, R$^b$, COR$^b$, OR$^b$, OCOR$^b$, OR$^b$-alkyl, S(O)$_m$R$^b$ wherein m is 0, 1 or 2 and R$^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl and m is 0, 1 or 2, SO₂NR$^d$R$^e$, wherein R$^d$ and R$^e$ independently are hydrogen, lower alkyl or R$^b$ as defined herein, NHR$^c$ or N(R$^c$)₂, wherein R$^c$ is as defined above;

the dotted lines (- - - -) represent optional double bonds in ring "M";

k is 0 or 1;

p is 0, 1, 2, 3, 4 or 5 provided that when Q is other than phenyl p is 0;

A is hydrogen, alkyl having from 1 to 6 carbon atoms, CH₂CH₂OH, COR$^f$, SO₂R$^f$ wherein R$^f$ is hydrogen, lower alkyl, phenyl or substituted phenyl, or (CH₂)$_q$R$^g$, wherein q is 1, 2, 3, 4 or 5 and R$^g$ is carboxyl or NR'₂, wherein R' is hydrogen or lower alkyl;

n is 2 to 6 provided that when n is 3, ring E has no double bond between carbon atoms;

each z is independently hydrogen, lower alkyl or z's on adjacent carbon atoms together form a double bond; and ring M is unsubstituted or substituted at its carbon atoms by lower alkyl groups.

2. A compound according to claim 1, wherein the compound is of the formula

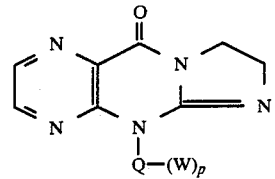

wherein Q, W and p are as defined in claim 1.

3. A compound according to claim 1, wherein the compound is of the formula

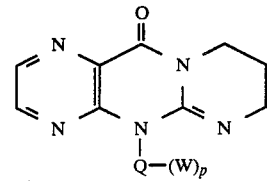

wherein Q, W and p are as defined in claim 1.

4. A compound as defined in claim 1 which is:
10-phenyl-2,3-dihydroimidazo[1,2-a]pyrazino[2,3-d]pyrimidin-5(10H)-one;
10-(3-methoxyphenyl)-2,3-dihydroimidazo[1,2-a]pyrazino[2,3-d]pyrimidin-5(10H)-one;
10-(3-chlorophenyl)-2,3-dihydroimidazo[1,2-a]pyrazino[2,3-d]pyrimidin-5(10H)-one;
10-(3,4-dichlorophenyl)-2,3-dihydroimidazo[1,2-a]pyrazino[2,3-d]pyrimidin-5(10H)-one;
10-(3-nitrophenyl)-2,3-dihydroimidazo[1,2-a]pyrazino[2,3-d]pyrimidin-5(10H)-one;
11-phenyl-2,3,4,11-tetrahydropyrimido[1,2-a]pyrazino[2,3-d]pyrimidin-6(6-H)-one;
11-(3-nitrophenyl)-2,3,4,11-tetrahydropyrimido-[1,2-a]pyrazino[2,3-d]pyrimidin-6(6H)-one; or
a pharmaceutically acceptable solvate, hydrate or salt thereof.

5. A compound having the structural formula Ia:

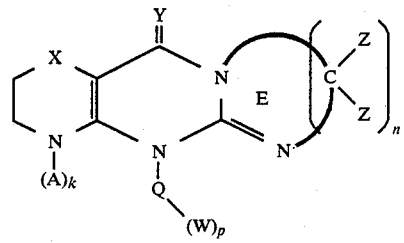

or a pharmaceutically acceptable solvate, hydrate or salt thereof, wherein:

X is CH₂;

Y is O or S;

Q is phenyl, pyridyl, furyl, thienyl, pyrrolyl, isoxazolyl, isothiazolyl or pyrazolyl;

W is lower alkyl, hydroxyl, halogen, nitro, amino, lower alkoxy, R¹, OR$^a$, NHR$^a$ wherein R$^a$ is acyl having from 1 to 6 carbon atoms, R$^b$, COR$^b$, OR$^b$, OCOR$^b$, OR$^b$-alkyl, S(O)$_m$R$^b$ wherein m is 0, 1 or 2 and R$^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl and m is 0, 1 or 2, SO₂NR$^d$R$^e$, wherein R$^d$ and $R^e$ independently are hydrogen, lower alkyl or $R^b$ as defined herein, $NHR^c$ or $N(R^c)_2$, wherein $R^c$ is as defined above;

k is 0 or 1;

p is 0, 1, 2, 3, 4 or 5 provided that when Q is other than phenyl p is 0;

A is hydrogen, alkyl having from 1 to 6 carbon atoms, $CH_2CH_2OH$, $COR^f$, $SO_2R^f$ wherein $R^f$ is hydrogen, lower alkyl, phenyl or substituted phenyl, or $(CH_2)_qR^g$, wherein q is 1, 2, 3, 4 or 5 and $R^g$ is carboxyl or $NR'_2$, wherein R' is hydrogen or lower alkyl;

n is 2 to 6 provided that when n is 3, ring E has no double bond between carbon atoms;

each z is independently hydrogen, lower alkyl or z's on adjacent carbon atoms together form a double bond; and ring M is unsubstituted or substituted at its carbon atoms by lower alkyl groups.

6. A compound defined in claim 5 which is:
10-phenyl-2,3,6,7,8,9-hexahydroimidazo[1,2-a]pyrido[2,3-d]pyrimidin-5(10H)-one or a pharmaceutically acceptable solvate, hydrate or salt thereof.

7. A compound defined in claim 5 wherein X is CH and Y is S.

8. A compound defined in claim 1 wherein X is N and Y is O.

9. 10-(3-Nitrophenyl)-2,3-dihydroimidazo[1,2-a]pyrazino[2,3-d]pyrimidine-5(10H)-one.

10. A method of treating allergy in a mammal comprising administering an anti-allergic effective amount of a compound having the formula I:

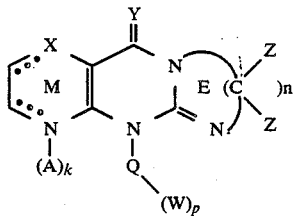

I or a pharmaceutically acceptable solvate, hydrate or salt thereof, wherein:

X is CH, $CH_2$, N or $N(A)_k$;

Y is O or S;

Q is phenyl, pyridyl, furyl, thienyl, pyrrolyl, isoxazolyl, isothiazolyl or pyrazolyl;

W is lower alkyl, hydroxy, halogen, nitro, amino, lower alkoxy, $R^a$, $OR^a$, $NHR^a$ wherein $R^a$ is acyl having from 1 to 6 carbon atoms, $R^b$, $COR^b$, $OR^b$, $OCOR^b$, $OR^b$-alkyl, $S(O)_mR^b$ wherein m is 0, 1 or 2 and $R^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, $S(O)_mR^c$, wherein $R^c$ is lower alkyl and m is 0, 1 or 2, $SO_2NR^dR^e$, wherein $R^d$ and $R^e$ independently are hydrogen, lower alkyl or $R^b$ as defined herein, $NHR^c$ or $N(R^c)_2$, wherein $R^c$ is as defined above;

the dotted lines (- - - - -) represent optional double bonds in ring "M";

k is 0 or 1;

p is 0, 1, 2, 3, 4 or 5 provided that when Q is other than phenyl p is 0;

A is hydrogen, alkyl having from 1 to 6 carbon atoms, $CH_2CH_2OH$, $COR^f$, $SO_2R^f$ wherein $R^f$ is hydrogen, lower alkyl, phenyl or substituted phenyl, or $(CH_2)_qR^g$, wherein q is 1, 2, 3, 4 or 5 and $R^g$ is carboxyl or $NR'_2$, wherein R' is hydrogen or lower alkyl;

n is 2 to 6 provided that when n is 3, ring E has no double bond between carbon atoms;

each z is independently hydrogen, lower alkyl or z's on adjacent carbon atoms together form a double bond, and ring M is unsubstituted or substituted at its carbon atoms by lower alkyl groups.

11. The method of claim 10 wherein the compound administered is:

10-phenyl-2,3-dihydroimidazo[1,2-a]pyrido[2,3-d]pyrimidin-5(10H)-one;

10-(3-methoxyphenyl)-2,3-dihydroimidazo[1,2-a]pyrido[2,3-d]pyrimidin-5(10H)-one;

10-(3-chlorophenyl)-2,3-dihydroimidazo[1,2-a]pyrido[2,3-d]pyrimidin-5(10H)-one;

10-(3,4-dichlorophenyl)-2,3-dihydroimidazo[1,2-a]pyrido[2,3-d]pyrimidin-5(10H)-one;

10-phenyl-2,3-dihydroimidazo[1,2-a]pyrazino[2,3-d]pyrimidin-5(10H)-one;

10-(3-methoxyphenyl)-2,3-dihyroimidazo[1,2-a]pyrazino[2,3-d]pyrimidin-5(10H)-one;

10-(3-chlorophenyl)-2,3-dihydroimidazo[1,2-a]pyrazino[2,3-d]pyrimidin-5(10H)-one;

10-(3,4-dichlorophenyl)-2,3-dihydroimidazo[1,2-a]pyrazino[2,3-d]pyrimidin-5(10H)-one;

10-(3-nitrophenyl)-2,3-dihydroimidazo[1,2-a]pyrido[2,3-d]pyrimidin-5(10H)-one;

11-phenyl-2,3,4,11-tetrahydropyrido[2,3-d]pyrimido[1,2-a]pyrimidin-6(6H)-one;

11-(3-methoxyphenyl)-2,3,4,11-tetrahydropyrido[2,3-d]pyrimido[1,2-a]pyrimidin-6(6H)-one;

11-(3-chlorophenyl)-2,3,4,11-tetrahydropyrido[2,3-d]pyrimido[1,2-a]pyrimidin-6(6H)-one;

11-(3-nitrophenyl)-2,3,4,11-tetrahydropyrido[2,3-d]pyrimido[1,2-a]pyrimidin-6(6H)-one;

11-(3,4-dichlorophenyl)-2,3,4,11-tetrahydropyrido[2,3-d]pyrimido[1,2-a]pyrimidin-6(6H)-one;

10-(4-hydroxyphenyl)-2,3-dihydroimidazo[1,2-a]pyrido[2,3-d]pyrimidin-5(10H)-one;

11-phenyl-2,3,4,11-tetrahydropyrimido[1,2-a]pyrazino[2,3-d]pyrimidin-6(6H)-one;

11-(3-nitrophenyl)-2,3,4,11-tetrahydropyrimido[1,2-a]pyrazino[2,3-d]pyrimidin-6(6H)-one;

10-(3-pyridyl)-2,3-dihydroimidazo[1,2-a]pyrido[2,3-d]pyrimidin-5(10H)-one;

10-phenyl-2,3-dihydroimidazo[1,2-a]pyrido[2,3-pyrimidin-5-(10H)-thione;

10-phenyl-2,3,6,7,8,9-hexahydroimidazo[1,2-a]pyrido[2,3-d]pyrimidin-5(10H)-one;

10-phenyl-imidazo[1,2-a]pyrido[2,3-d]pyrimidin-5(10H)-one;

12-phenyl-2,3,4,5-tetrahydropyrido[2',3':4,5-]pyrimidin[1,2-a][1,3]diazepine-7(12H)-one; or a pharmaceutically acceptable solvate, hydrate or salt thereof.

12. A method of treating inflammation in a mammal comprising administering to said mammal an anti-inflammatory effective amount of a compound of formula I

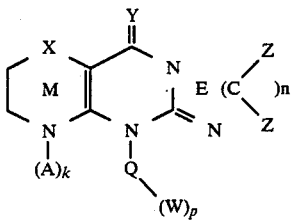

or a pharmaceutically acceptable solvate, hydrate or salt thereof, wherein:

X is CH, CH$_2$, N or N(A)$_k$;

Y is O or S;

Q is phenyl, pyridyl, furyl, thienyl, pyrrolyl, isoxazolyl, isothiazolyl or pyrazolyl;

W is lower alkyl, hydroxyl, halogen, nitro, amino, lower alkoxy, R$^a$, OR$^a$, NHR$^a$ wherein R$^a$ is acyl having from 1 to 6 carbon atoms, R$^b$, COR$^b$, OR$^b$, OCOR$^b$, OR$^b$-alkyl, S(O)$_m$R$^b$ wherein m is 0, 1 or 2 and R$^b$ is phenyl, naphthyl, indenyl, indanyl, phenanthridinyl, pyridyl, pyrimidyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl and m is 0, 1 or 2, SO$_2$NR$^d$R$^e$, wherein R$^d$ and R$^e$ independently are hydrogen, lower alkyl or R$^b$ as defined herein, NHR$^c$ or N(R$^c$)$_2$, wherein R$^c$ is as defined above;

the dotted lines (- - - -) represent optional double bonds in ring "M";

k is 0 or 1;

p is 0, 1, 2, 3, 4 or 5 provided that when Q is other than phenyl p is 0;

A is hydrogen, alkyl having from 1 to 6 carbon atoms, CH$_2$CH$_2$OH, COR$^f$, SO$_2$R$^f$ wherein R$^f$ is hydrogen, lower alkyl, phenyl or substituted phenyl, or (CH$_2$)$_q$R$^g$, wherein q is 1, 2, 3, 4 or 5 and R$^g$ is carboxyl or NR'$_2$, wherein R' is hydrogen or lower alkyl;

n is 2 to 6 provided that when n is 3, ring E has no double bond between carbon atoms;

each z is independently hydrogen, lower alkyl or z's on adjacent carbon atoms together form a double bond, and ring M is unsubstituted or substituted at its carbon atoms by lower alkyl groups.

13. A method for treating hyperproliferative skin disease in a mammal comprising topically administering to said mammal an effective amount of a compound of formula I

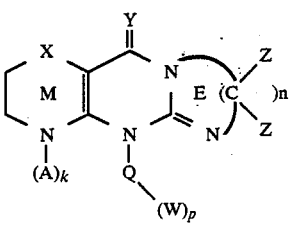

or a pharmaceutically acceptable solvate, hydrate or salt thereof, wherein:

X is CH, CH$_2$, N or N(A)$_k$;

Y is O or S;

Q is phenyl, pyridyl, furyl, thienyl, pyrrolyl, isoxazolyl, isothiazolyl or pyrazolyl;

W is lower alkyl, hydroxyl, halogen, nitro, amino, lower alkoxy, R$^a$, OR$^a$, NHR$^a$ wherein R$^a$ is acyl having from 1 to 6 carbon atoms, R$^b$, COR$^b$, OR$^b$, OCOR$^b$, OR$^b$-alkyl, S(O)$_m$R$^b$ wherein m is 0, 1 or 2 and R$^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl and m is 0, 1 or 2, SO$_2$NR$^d$R$^e$, wherein R$^d$ and R$^e$ independently are hydrogen, lower alkyl or R$^b$ as defined herein, NHR$^c$ or N(R$^c$)$_2$, wherein R$^c$ is as defined above;

the dotted lines (- - - -) represent optional double bonds in ring "M";

k is 0 or 1;

p is 0, 1, 2, 3, 4 or 5 provided that when Q is other than phenyl p is 0;

A is hydrogen, alkyl having from 1 to 6 carbon atoms, CH$_2$CH$_2$OH, COR$^f$, SO$_2$R$^f$ wherein R$^f$ is hydrogen, lower alkyl, phenyl or substituted phenyl, or (CH$_2$)$_q$R$^g$, wherein q is 1, 2, 3, 4 or 5 and R$^g$ is carboxyl or NR'$_2$, wherein R' is hydrogen or lower alkyl;

n is 2 to 6 provided that when n is 3, ring E has no double bond between carbon atoms;

each z is independently hydrogen, lower alkyl or z's on adjacent carbon atoms together form a double bond, and ring M is unsubstituted or substituted at its carbon atoms by lower alkyl groups.

14. A method for suppressing the immune response in a mammal comprising administering to said mammal an immunosuppressive effective amount of a compound of formula I

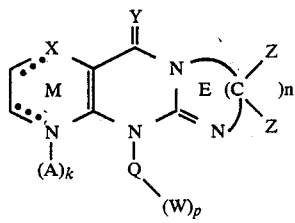

or a pharmaceutically acceptable solvate, hydrate or salt thereof, wherein:

X is CH, CH$_2$, N or N(A)$_k$;

Y is O or S;

Q is phenyl, pyridyl, furyl, thienyl, pyrrolyl, isoxazolyl, isothiazolyl or pyrazolyl;

W is lower alkyl, hydroxyl, halogen, nitro, amino, lower alkoxy, R$^a$, OR$^a$, NHR$^a$ wherein R$^a$ is acyl having from 1 to 6 carbon atoms, R$^b$, COR$^b$, OR$^b$, OCOR$^b$, OR$^b$-alkyl, S(O)$_m$R$^b$ wherein m is 0, 1 or 2 and R$^b$ is phenyl, naphthyl, indenyl, indanyl, phenanthridinyl, pyridyl, pyrimidyl, pyrazinyl, pyridazinyl, 1,2,4-triazinyl, furyl, thienyl, pyrrolyl, benzofuranyl, indolyl, imidazolyl, pyrazolyl, triazolyl or thiazolyl, SH, S(O)$_m$R$^c$, wherein R$^c$ is lower alkyl alkyl and m is 0, 1 or 2, SO$_2$NR$^d$R$^e$, wherein R$^d$ and R$^e$ independently are hydrogen, lower alkyl or R$^b$ as defined herein, NHR$^c$ or N(R$^c$)$_2$, wherein R$^c$ is as defined above;

the dotted lines (- - - -) represent optional double bonds in ring "M";

k is 0 or 1;

p is 0, 1, 2, 3, 4 or 5 provided that when Q is other than phenyl p is 0;

A is hydrogen, alkyl having from 1 to 6 carbon atoms, $CH_2CH_2OH$, $COR^f$, $SO_2R^f$ wherein $R^f$ is hydrogen, lower alkyl alkyl, phenyl or substituted phenyl, or $(CH_2)_qR^g$, wherein q is 1, 2, 3, 4 or 5 and $R^g$ is carboxyl or $NR'_2$, wherein $R'$ is hydrogen or lower alkyl;

n is 2 to 6 provided that when n is 3, ring E has no double bond between carbon atoms;

each z is independently hydrogen, lower alkyl or z's on adjacent carbon atoms together form a double bond, and ring M is unsubstituted or substituted at its carbon atoms by lower alkyl groups.

* * * * *